United States Patent [19]

Bodicky

[11] Patent Number: 4,540,411

[45] Date of Patent: Sep. 10, 1985

[54] CATHETER PLACEMENT DEVICE

[75] Inventor: Raymond O. Bodicky, Oakville, Mo.

[73] Assignee: Sherwood Medical Company, St. Louis, Mo.

[21] Appl. No.: 555,862

[22] Filed: Nov. 28, 1983

[51] Int. Cl.³ .............................................. A61M 5/00
[52] U.S. Cl. ................................... 604/169; 604/250; 251/4
[58] Field of Search ............... 604/169, 164, 246, 34, 604/250; 251/4

[56] References Cited

U.S. PATENT DOCUMENTS

| | | | |
|---|---|---|---|
| 2,416,391 | 2/1947 | Hixon | 604/405 |
| 2,844,351 | 7/1958 | Smith | 604/250 |
| 3,304,934 | 2/1967 | Bautista | 128/766 |
| 3,329,390 | 7/1967 | Hulsey | 251/4 |
| 3,599,637 | 8/1971 | Schwartz . | |
| 4,016,879 | 4/1977 | Mellor | 604/169 |
| 4,063,555 | 12/1977 | Ulinder . | |
| 4,243,034 | 1/1981 | Brandt | 604/169 |
| 4,311,137 | 1/1982 | Gerard . | |

OTHER PUBLICATIONS

Mucon, "Iris Diaphragm Valves", KEK Inc., Bristol, Pa.

Primary Examiner—Stephen C. Pellegrino
Attorney, Agent, or Firm—Stanley N. Garber; William R. O'Meara

[57] ABSTRACT

A catheter placement device is provided which includes a catheter, a pair of relatively rotatable valve members connected to the catheter, an elastomeric longitudinally extending tubular member connected between the valve members and twistable in response to relative rotation of the valve members, and an introducer needle extending longitudinally through the tubular member and catheter for introducing the distal end of the catheter into a blood vessel. Predetermined relative rotation between the valve members effects twisting of the tubular member about the needle and closure of the tubular member. A side port may be connected to a valve member for introducing fluid into a patient.

18 Claims, 7 Drawing Figures

CATHETER PLACEMENT DEVICE

DESCRIPTION

1. Technical Field

This invention relates to catheter placement devices and more particularly to a cathether placement device which can be used for the infusion of fluids or removal of fluids from a patient.

2. Background Art

Catheter placement devices generally include a plastic catheter and an introducer needle which extends through the catheter with its pointed end beyond the distal end of the catheter for inserting the catheter and needle into a body vessel such as an artery or vein of a patient. After proper placement, the needle is removed from the catheter while the catheter remains in the vessel. The proximal end of the catheter may be provided with a connector for receiving a syringe or other device for removing blood from the patient or for introducing a medicament, or for connecting the catheter to an infusion system having a source of intravenous liquid.

There have been certain problems associated with infusion systems. For example, connecting an infusion liquid source to the catheter is relatively tedious and may result in excessive blood and infusion liquid escaping. These steps generally require a considerable amount of manipulation of the catheter placement device while a catheter is in the vein of the patient, and this tends to increase the danger to the patient of damage from the needle as well as discomfort.

In U.S. Pat. No. 3,599,637, an intravenous catheter assembly is disclosed which reduces or prevents spillage. In this patent, a resilient tubular member such as of soft rubber is connected between the infusion liquid system and the catheter hub. The tubular member is bent at an angle to the catheter. After insertion of the needle and catheter, the needle is removed and infusion liquid allowed to enter the patient through the catheter. One of the disadvantages of this type of placement device is that the needle must cut through the resilient tubular member which may cause coring and the possibility that a fragment of the resilient member may enter the patient. Also, there is the additional step of inserting the needle into the tubular member before insertion into the patient. This requires separate and additional packaging and handling of the needle. On the other hand, if the needle is inserted into the catheter at the factory and remains in the resilient tubular member during storage, the hole caused by the needle tends to remain open after the needle is removed since the material tends to take a permanent set during storage. This would result in possible leakage during use.

In U.S. Pat. No. 4,311,137, a fluid administration or catheter placement device is disclosed which has a seal pierced by an introducer needle which may be stored in that condition so as to be ready for use without requiring insertion of the needle at the time of use. However, in order to avoid the possibility that the hole through which the needle extends will remain partially open when the needle is removed, the device is made so that the seal is shifted into a compressed condition at the time of use to insure that the seal will not leak. This, however, adds to the complexity and cost of the device.

DISCLOSURE OF THE INVENTION

It is therefore an object of the present invention to provide an improved catheter placement device which is relatively inexpensive and simple to use, and which overcomes one or more of the abovementioned problems.

A more specific object is to provide an improved catheter placement device having a member for closing a passage wherein an introducer needle can be stored in place within an introducer catheter and a passage closure member without effecting the reliability of the closure member and without the danger of coring.

Still another object is to provide an improved catheter placement device of the above-mentioned type wherein an infusion liquid source can be connected with the device and air removed prior to insertion of the catheter and needle into the body of a patient.

In accordance with one aspect of the present invention, a catheter placement device is provided which includes a catheter, a valve including a pair of relatively rotatable valve members, and a flexible tubular member having opposed ends respectively connected to the valve members, and an introducer needle insertable longitudinally through the tubular member and the catheter for inserting the catheter into a body. The tubular member is twistable about the needle in response to predetermined relative rotation between the valve members to close the tubular member.

These as well as other objects and advantages of the present invention will be apparent from the detailed description and accompanying drawing.

DETAILED DESCRIPTION OF THE PREFERRED EMBODIMENTS

Figure 1:
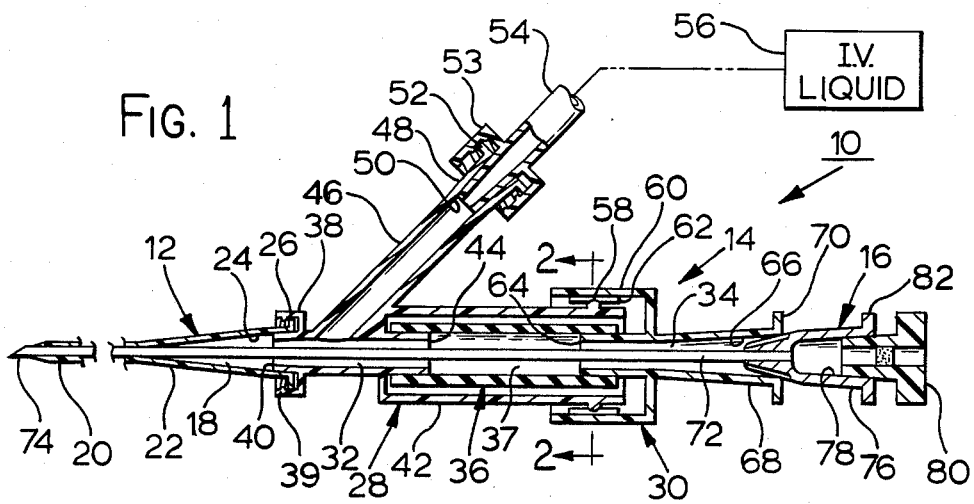
FIG. 1 is a longitudinal cross-sectional view of a catheter placement device in accordance with a preferred embodiment of the present invention.

Referring now to the drawing, and particularly to FIG. 1, a catheter placement device for the infusion of a medical fluid into the body of a patient is indicated generally at 10. Device 10 is shown including a catheter 12, a valve assembly 14, and an introducer needle assembly 16.

Catheter 12 is shown having a lumen 18, a relatively narrow distal end 20 adapted for insertion into a blood vessel such as an artery or vein of a patient, and an intregal hub 22 in the form of a female Luer lock connector connecting the catheter 12 with the valve assembly 14. Hub 22 is in the form of a Luer lock connector that includes a Luer tapered bore 24 and a pair of diametrically opposed coupling thread members or radially extending ears 26. Catheter 12 may be formed of a plastic such as Teflon, Nylon, polyethylene, or other suitable thermoplastic material.

The valve assembly 14 includes a pair of relatively rotatable valve members 28 and 30 having bores or passages 32 and 34, respectively, and a flexible tubular member 36 having a bore or passage 37 connected in series flow relation between the valve member bores. The passage 37 extends longitudinally and has opposed coaxial ends open for fluid communication with the bores 32 and 34.

Valve member 28 includes an intregal Luer lock connector 38 at its distal end. Connector 38 includes a Luer tapered male member 40 which is frictionally received in Luer tapered bore 24 of hub 22. Connector 38 includes an internally threaded collar 39 surrounding Luer member 40 and which threadedly receives the ears 26 of the catheter hub 22. When valve member 28 and catheter 12 are rotated relative to each other, the Luer member 40 is urged into tight sealing engagement with the bore 24 to connect the lumen 18 in fluid communication with the bore 32 of the valve member 28. Where desired, instead of mechanically connecting the catheter to member 28 by employing the complementary Luer connectors 22 and 38 as shown, the catheter 12 and member 28 may be integrally formed as a single piece without the Luer connectors.

Figure 2:
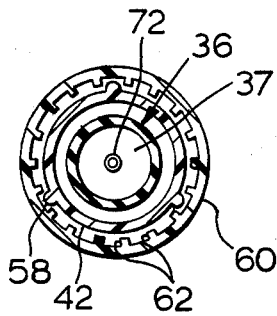
FIG. 2 is an enlarged cross-sectional view taken along line 2—2 of FIG. 1.

Valve member 28 has an axially extending, generally cylindrical collar 42 at its proximal end and an inner cylindrical extension collar 44 radially spaced from collar 42. The distal end portion of tubular member 36 extends over extension 44 and into the annular space between the collar 42 and extension 44 and is connected to extension 44 such as by adhesively bonding or mechanically affixing it to the extension. Valve member 28 also has a side port 46 having a female Luer lock connector 48 which includes a Luer tapered bore 50 and a pair of radial ears 52. Connector 48 is shown connected in fluid tight connection with a male Luer lock connector 48 is shown connected in fluid tight connection with a male Luer lock connector 53 connected at the end of infusion fluid tubing 54 which is shown connected to a source 56 of an intravenious (IV) solution. Outer collar 42 is provided with a plurality of equally circumferentially spaced, radially outwardly extending, rounded abutments 58, as also seen in FIG. 2 and which will be further explained hereafter.

Valve member 30 includes an outer cylindrical collar 60 which receives the distal end portion of valve member 28 in telescopic relation. Collar 60 has internal, circumferentially spaced, axially extending radial abutments or splines 62 on its inner wall that are engageable with the abutments 58 on valve member 28 to allow relative rotation of the valve members 28 and 30 when desired, and to maintain them in the selected relative relationship. Valve member 30 also includes an inner cylindrical extension 64 radially spaced from collar 60. The proximal end of tubular member 36 is received in the space between collar 60 and extension 64 and is secured to extension 64 such as by heat bonding, adhesively cementing or mechanically affixing it to the extension. Connected to the bore 34 of valve member 30 is a Luer tapered bore 66 of an integral female Luer lock connector 68 at the proximal end of valve member 30. Connector 68 has a Luer lock collar with radial ears 70. The catheter lumen 18, bore 32 of valve member 28, passage 37 of tubular member 36, and the bore 34 of valve member 30 are all shown connected in aligned or coaxial relationship.

Needle assembly 16 includes a hollow hypodermic needle or needle cannula 72 having a pointed end 74 and which extends through the bores 32 and 34 of the valve members, passage 37 of tubular member 36 and the lumen 18 of catheter 12. The distal pointed tip 74 extends beyond the distal end of catheter 12 for inserting the needle and catheter into a blood vessel such as a vein of a patient. Needle assembly 16 is provided with a needle hub 76 at its proximal end. The needle hub 76 is in the form of a Luer lock connector provided with a Luer tapered bore 78 which is shown receiving a conventional hydrophobic filter member 80 that allows air but not blood to flow through it. A pair of diametrically opposed radial Luer lock ears 82 are provided on the end of the needle hub.

Figure 3:
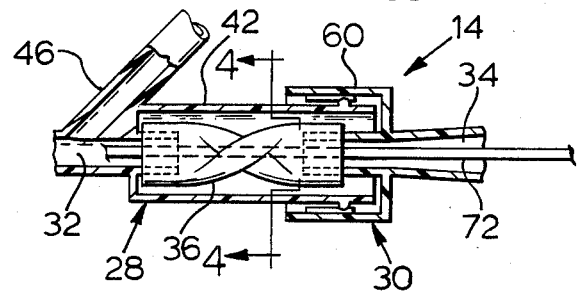
FIG. 3 is a longitudinal cross-sectional view of a portion of the device of FIG. 1 but after relative rotation between valve members of the device has occurred.
Figure 4:
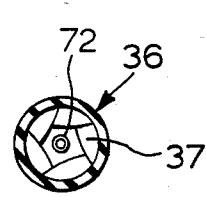
FIG. 4 is an enlarged cross-sectional view taken along the line 4—4 of FIG. 3.
Figure 5:
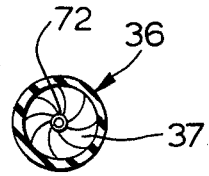
FIG. 5 is an enlarged cross-sectional view similar to FIG. 4 but, illustrating the device after the valve members have been further relatively rotated.
Figure 6:
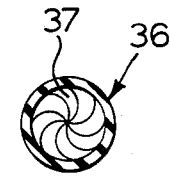
FIG. 6 is an enlarged cross-sectional view similar to FIG. 5 but with the needle removed from the device.

The flexible tubular member 36 of the valve assembly 14 is preferably formed of an elastomeric material such as natural or synthetic rubber or a soft flexible and resilient thermoplastic material, for example, a soft silicone or isoprene rubber or other elastomeric material. The tubular member 36 is twistable about its longitudinal axis in response to relative rotation between the valve members 28 and 30. In FIG. 3, the tubular member 36 is shown twisted as a result of a given amount of relative rotation between the valve members 28 and 30. As seen in FIG. 4, a portion of passage 37 intermediate its ends has been reduced in size or cross-section. If the relative rotation of members 28 and 30 exceeds a predetermined amount, the walls of the passage at the intermediate portion will engage the outer surface of the sidewalls of needle 72 and completely close the passage 37 about the needle, the condition illustrated in FIG. 5. If, after closing the passage 37, as in FIG. 5, the needle 72 is removed from the catheter 18 and valve assembly 14, the passage 37 will remain closed as illustrated in FIG. 6. Thus, the intermediate portion or center of passage 37 forms an orifice which can be varied in size from the fully open condition as in FIGS. 1 and 2 to the fully closed conditions as in FIGS. 5 and 6. The dimensions of the tubular valve member and the material from which it is made will have an affect on the amount of relative rotation between the valve members 28 and 30 that is necessary to close the orifice or passage 37 of the tubular member 36.

The catheter placement device 10 may be packaged in the condition shown, that is with needle 72 extending longitudinally or axially through bores 32 and 34 of the valve members and the passage 37 of the tubular member 36. As shown, the needle 72 is concentric and coaxial with the tubular member passage 37 and, of course, does not penetrate or cut through the material or sidewalls of the tubular member but passes through the open ends of the tubular member. In this way, no separate packaging and connecting or needle insertion steps are necessary to prepare the device 10 for use. Also, there is no danger of coring the elastomeric material when placing the device in use.

In use, and when it is desired to effect intravenous infusion of a solution, the device 10 is unpackaged in sterile condition and the port 46 may be connected to tubing 54 which may be initially closed by a suitable clamp (not shown). This connection is made by means of the Luer lock connectors 48 and 53. The clamp may then be opened so that fluid is allowed to flow into the lumen 18, bores 32 and 34, and passage 37 so as to remove air from the interior portions of the device. Air escapes from the proximal end of bore 34 since the needle hub 76 is not in air-tight fitting relation with bore 34. After air has been removed from the interior portions of the device 10, the valve members 28 and 30 may be relatively rotated such as by holding valve member 28 stationary while rotating valve member 30 a predetermined amount to twist the flexible, elastomeric tubular member 36 sufficiently about the longitudinal axis of the device to close passage 37 of the tubular member about the needle 72, such as indicated in FIG. 5. the distal tip of the needle 74 is then passed through the skin and into a blood vessel such as a vein. If successful venipuncture has occured, blood will flow through the needle into bore 78 of the needle hub 76 with air escaping through filter member 80. With the valve assembly 14 closed, the needle may be removed from the device and discarded. The tubular member 36 will maintain the passage 37 closed as in FIG. 6 so that infusion liquid is administered through port 46 and catheter 12 into the vein of the patient. The device 10 may be taped to the body of the patient to maintain catheter 18 in its desired position.

During relative rotation between valve members 28 and 30, the splines 62 engage and pass over the rounded abutments 58 with the abutments entering spaces between adjacent splines such as indicated in FIG. 2. When turning effort is stopped, the abutments 58 will be disposed in spaces between splines and maintain the valve members 28 and 30 in the selected relative relationship. The valve members may be molded or formed of any suitable relativly hard plastic for example, polyethylene, but which is flexible enough to allow relative rotation of the two members when a manually applied torque is applied and yet provide sufficient resistance so that the members will stay in any given relative rotational position opposing any return forces due to the resiliency of the elastomeric tubular member 36.

Because the infusion solution from source 56 can be connected to port 46 prior to insertion of the device into the blood vessel, the chance of inadverdant damage to the patient by the needle due to manipulation of parts during connection of the device with the infusion tubing 54 is reduced.

Where desired, the valve assembly 14 may be reopened such as by rotating the valve member 30 relative to valve member 28 in a direction opposite to that required to close the valve assembly. In this way, the tubular sleeve member 36 is untwisted or returned to its open condition such as shown in FIGS. 1 and 2. The valve assembly 14 may be reopened, for example, for the purpose of introducing a liquid medicament such as by use of a syringe or a Luer conncetor from another IV liquid source. For example, a syringe tip having a Luer tapered surface may be inserted in fluid tight relation into the Luer tapered bore 66 of the valve member 30 and a liquid medicament moved through the bore 34, tubular member 36 and the catheter 12 into the blood vessel. This may be done with or without stopping the supply of infusion liquid to port 46. After such infusion, the valve members may again be relatively rotated to close the valve assembly as previously discussed. Thus, the valve assembly 14 makes it convenient to introduce medicaments or liquids without the necessity of additional venipuncture, and without stopping infusion flow from the port 46.

Figure 7:
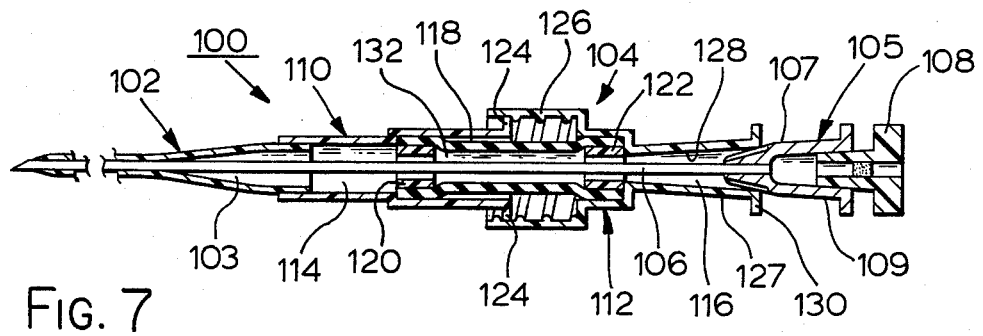
FIG. 7 is a longitudinal cross-sectional view of a modified embodiment of the present invention.

A modified catheter placement device is indicated generally at 100 in FIG. 7. Device 100 includes an introducer catheter 102 having a lumen 103 and which is connected to the distal end of a valve assembly 104 such as by adhesively bonding adjacent ends of the catheter 102 and member 104 together or mechanically securing them together. Also, they may be molded together as a single piece so that an intergral portion of the piece connects them together. If desired, the catheter 102 and valve 104 may be provided with complementary connectors as in the device 10. The device 100 includes an introducer needle assembly 105 having a metal needle cannula 106. Neddle 106 is shown extending longitudinally through the valve assembly 104 and catheter 102 with its distal pointed end extending beyond the distal end of the catheter. The needle assembly has a hub 107 which receives a hydrophobic filter 108 and has an integral Luer lock connector 109 at the proximal end.

Valve assembly 104 includes relatively rotatable valve members 110 and 112 having through bores 114 and 116, respectively, and an open-ended, flexible sleeve or tubular member 118 which is preferably of an elastomeric material. The opposite ends of the tubular 118 are provided with supporting rings 120 and 122 that may be cemented or mechanically affixed to the tubular member for stiffening the ends of the tubular member so that the outer surface of the opposite ends of the tubular member can be mechanically affixed or adhesively secured to the inner walls of valve members 110 and 112, respectively.

The valve member 110 has a pair of diametrically opposed Luer lock type ears 124 extending radially outwardly at the proximal end of the valve member and which are threadedly received in an internally threaded Luer lock collar 126 of valve member 112. The proximal end portion of valve member 112 is provided with a Luer lock connector 127 having a Luer tapered socket 128 and Luer lock ears 130. The tubular member 118 has an open-ended passage or bore 132 which is shown coaxial with needle 106, bores 114 and 116 of the valve members, and with the lumen 103 of catheter 102. The needle 106 passes longitudinally through the open ends of the tubular members and, of course, does not cut through the sidewalls of the member.

In use, the distal ends of needle 106 and catheter 102 may be inserted through the skin and into the vein of a patient. The catheter is then moved so that the distal tip is in a desired location within the vein. The needle assembly 105 is removed from the device with blood then flowing into the catheter lumen 103 and bores 114 and 116 removing the air from device 100. The valve members 110 and 112 are then relatively rotated, for example, by holding member 110 stationary and rotating valve 112. The collar 126 of valve member 112 is threaded past ears 124 until the valve members are in tight frictional holding engagement with each other. The distance threaded or relative rotation effected is sufficient to cause the tubular member 118 to become fully twisted about the needle 106 to close the intermediate portion or orifice in passage 132 so that no fluid, blood or infusion liquid can flow through the passage 132 or between the bores 114 and 116. With the tubular member 118 tightly and resiliently engaging the outer surface of needle 106, the needle assembly 105 can be withdrawn from the catheter 102 and valve members 110 and 112 and the needle assembly discarded. Because of the resilience and twisted engagement between the tubular member 118 and the sidewalls of needle 106, the tubular member passage 132 remains completely closed after removal of the needle 106 from the device.

With the needle assembly 105 removed and the tubular member 118 closed, a Luer lock connector of an infusion liquid supply tube (such as a connector similar to Luer Lock connector 53 of FIG. 1) can be inserted and threaded onto Luer lock connector 127 so that infusion fluid can flow into bore 116. After connection with the source of infusion liquid, the Luer lock connection between the valve members 110 and 112 can be reversed, that is, the direction of rotation of valve member 112 can be reversed from the direction of rotation that resulted in the closure of the passage 132 of the tubular member. This effects the untwisting of the tubular member 118 and the opening of the passage 132 for the flow of infusion liquid therethrough and through the catheter 102 and into the vein of the patient.

Closing the passage 132 of the twistable tubular member 118 after the venipuncture has been accomplished permits the person making the connection to the IV system or source of infusion liquid to do so in a simple and easy fashion and while avoiding or reducing spillage of liquids. Where desired, the infusion of liquid may be readily interrupted by effecting relative rotation of valve members 110 and 112 to close the passage 132. The valve passage 132 may be conviently closed and opened, for example, where infusion is to be interrupted and an additional liquid medicament is be injected such as by a syringe having its tip placed into the Luer bore 128 of member 112.

While the amount of relative rotation between the valve members 110 and 112 needed to close the passage 13 are affected by the length, and other dimensions of a tubular member 18, the tubular member should be dimensioned so that it is twisted sufficiently to close the passage 132 within the limits of the rotational connection of the ears 124 and threaded collar 126.

In both catheter placement devices 10 and 100 the opposite ends of elastomeric tubular member are fixed to relatively rotatable valve members so that it is stretched or stretched and shortened in length during the relative rotation of the valve members. The resiliency of tubular members tends to return them to their original or formed tubular shape when relieved of turning forces.

For purpose of example only, the tubular members 36 and 118 of the devices 10 and 100 may be formed of silicone rubber with an inner diameter of about 0.150 inch (0.381 cm), an outer diameter of about 0.200 inch (0.508 cm), and an effective length of about 0.300 inch (0.762 cm), the effective length being the axial length of the twistable portion of the tubular member. For example, the effective length is that between the facing surfaces of members 44 and 64 in FIG. 1 to which the ends of the tubular member 36 are secured. In general, the tubular member passage closes when one of the relatively rotatable valve members is rotated about 180 degrees relative to the other valve member.

Where desired the Luer tip of a syringe tip can be inserted into the needle hub (76,107) and the syringe used to withdraw blood from the vein, for example, for test purposes.

Because the introducer needle in each of the devices 10 and 100 does not cut through the material of any elastomeric member, no coring of material or introduction of cored material into the patient is possible. Also, since the needle does not cut through the tubular member material, the needle can be positioned in the present catheter placement device and packaged by the manufacturer such that the device is in condition for use upon removal from the package. The presence of the needle in the device during storage does not affect the characteristics of the elastomeric tubular member or its function in the valve since it does cut through an elastomeric member.

As various changes could be made in the above constructions without departing from the scope of the invention, it is intended that all matter contained in the above description and shown in the accompanying drawing shall be interpreted as illustrative and not in a limiting sense.

What is claimed is:

1. A catheter placement device comprising valve means including a pair of relatively rotatable valve members, a flexible tubular member having opposed end portions connected respectively to said valve members, said tubular member having inner sidewalls defining a passage therethrough and being twistable in response to relative rotation between said valve members to define a variable orifice in said passage, a catheter having a lumen, said catheter having one end portion adapted for insertion into a body and an opposite end portion adapted to connect said lumen in fluid communication with said passage, an introducer needle insertable through said passage and said lumen and retractable therefrom for introducing said catheter into the body, said sidewalls being engageable with and twistable about the sidewalls of said needle in response to predetermined relative rotation between said valve members to close said orifice about said needle to thereby close said passage, and cooperating means on said valve members for holding one of said valve members in any selected one of a plurality of different positions relative to the other of said valve members.

2. The device of claim 1 wherein said tubular member is of an elastomeric material.

3. The device of claim 1 wherein said cooperating means includes a plurality of abutment means on one of said valve members, and abutment means on the other of said valve members engageable with said first named abutment means.

4. The device of claim 1 wherein said cooperating means includes complementary thread means respectively on valve members.

5. The device of claim 1 wherein said tubular member is of an elastomeric material, and said needle is removable from said tubular member when said orifice is closed about said needle without opening said passage.

6. The device of claim 1 wherein said catheter is connected to one of said valve members, the other of said valve members includes connector means for connecting a source of fluid thereto.

7. The device of claim 6 further including a fluid port connected to said one valve member for connecting a source of fluid in fluid communication with said lumen.

8. The device of claim 6 wherein said connector means includes a Luer lock connector.

9. The device of claim 1 wherein each of said valve members has a passageway therethrough connecting with said tubular member passage so that said needle is insertable through said passage, lumen and passageways.

10. The device of claim 1 wherein each of said valve members has a passageway coaxial with said tubular member passage and said lumen.

11. A catheter placement device comprising valve means including distal and proximal relatively rotatable valve members each having a longitudinally extending passage therethrough, and an elastomeric tubular member having inner walls defining a longitudinally extending passage therethrough and opposed open end portions fixedly connected respectively to said distal and proximal members with said passages being coaxial, a catheter having a lumen therethrough, a distal end portion adapted for insertion into a body, and a proximal end portion for connection to said distal valve member with said lumen in fluid communication said tubular member passage, and a needle removably longitudinally insertable through said tubular member passage and open end portions thereof, through said valve member passages, and through said lumen wit the distal end thereof extending beyond the distal end of said catheter for inserting the distal ends of said catheter and needle into the body, said tubular member being twistable between the opposed end portions thereof and about said needle with said inner walls thereof engaging the outer surface of the sidewalls of said needle to close said tubular member passage about said needle in response to a predetermined amount of rotation of one of said valve members in one direction relative to the other of said valve members, said one valve member being rotatable relative to said other valve member to effect a corresponding variable orifice in said tubular member passage which varies in size from a maximum open condition when said one valve member is in a given position relative to said other valve member to a closed condition when said one member is rotated said predetermined amount from said given position relative to said other member, said valve members including complementary cooperating frictional engagement means for maintaining said one valve member in a selected position relative to said other valve member.

12. The device of claim 11 wherein said tubular member is sufficiently resilient to maintain said tubular member passage closed when said needle is proximally removed from said tubular member and valve member passages after said predetermined rotation of said one valve member.

13. The device of claim 12 wherein said one valve member is rotatable relative to said other valve member in a direction opposite said one direction to untwist said tubular member from a twisted condition in which said tubular member passage is closed to an untwisted condition in which said tubular member passage is open.

14. The device of claim 11 wherein said proximal valve member includes a Luer tapered connector at the proximal end thereof connectable to a source of infusion liquid for supplying the liquid to the body through said tubular member and valve member passages and said catheter lumen.

15. The device of claim 14 wherein said distal valve member includes a port connectable to a fluid device and connected in fluid communication with said passage thereof for the flow of fluid between said fluid device and said lumen.

16. The device of claim 11 wherein said frictional engagement means includes a plurality of circumferentially spaced first abutment members on one of said valve members, and second abutment means on the other of said valve members engageable with and movable past said abutment members when torque above a predetermined value is applied to one of said members while holding the other of said members stationary.

17. The device of claim 11 wherein portions of said valve members are disposed in concentric relation, and said cooperating frictional engagement means include first and second abutment means respectively disposed on the radially inner side of one of said valve member portions and on the radially outer side of the other of said valve member portions.

18. The device of claim 11 wherein one of said valve members includes a collar having first thread means on the inner surface thereof, and said other valve member has second thread means thereon threadedly engageable with said first thread means for locking said valve members in a relative position in which said passage is closed.

* * * * *